United States Patent [19]

Brennan et al.

[11] Patent Number: 4,480,145

[45] Date of Patent: Oct. 30, 1984

[54] CATALYSTS FOR THE CONVERSION OF METHANOL TO ETHYLENE PLUS GASOLINE

[75] Inventors: James A. Brennan, Cherry Hill; Stanley J. Lucki, Runnemede; Hans J. Schoennagel, Lawrenceville, all of N.J.

[73] Assignee: Mobil Oil Corporation, New York, N.Y.

[21] Appl. No.: 419,105

[22] Filed: Sep. 16, 1982

[51] Int. Cl.$^3$ .......................... C07C 2/68; B01J 29/28
[52] U.S. Cl. .................................... 585/640; 502/77; 585/408
[58] Field of Search .................. 252/455 Z; 585/640, 585/408; 502/77, 71

[56] References Cited

U.S. PATENT DOCUMENTS

| | | | |
|---|---|---|---|
| 4,016,218 | 4/1977 | Haag et al. | 585/467 |
| 4,025,575 | 5/1977 | Chang et al. | 585/640 |
| 4,300,011 | 11/1981 | Rollmann | 585/467 |
| 4,359,595 | 11/1982 | Rollmann | 585/640 |
| 4,429,176 | 1/1984 | Chester et al. | 585/640 X |

*Primary Examiner*—Carl F. Dees
*Attorney, Agent, or Firm*—A. J. McKillop; M. G. Gilman; J. F. Powers, Jr.

[57] ABSTRACT

A methanol conversion process in which a methanol feed is catalytically converted to ethylene and gasoline over a crystalline aluminosilicate zeolite catalyst which has been presteamed in order to adjust the alpha activity of the catalyst to about 6–100. Catalyst stability and cycle time on stream are increased.

10 Claims, 1 Drawing Figure

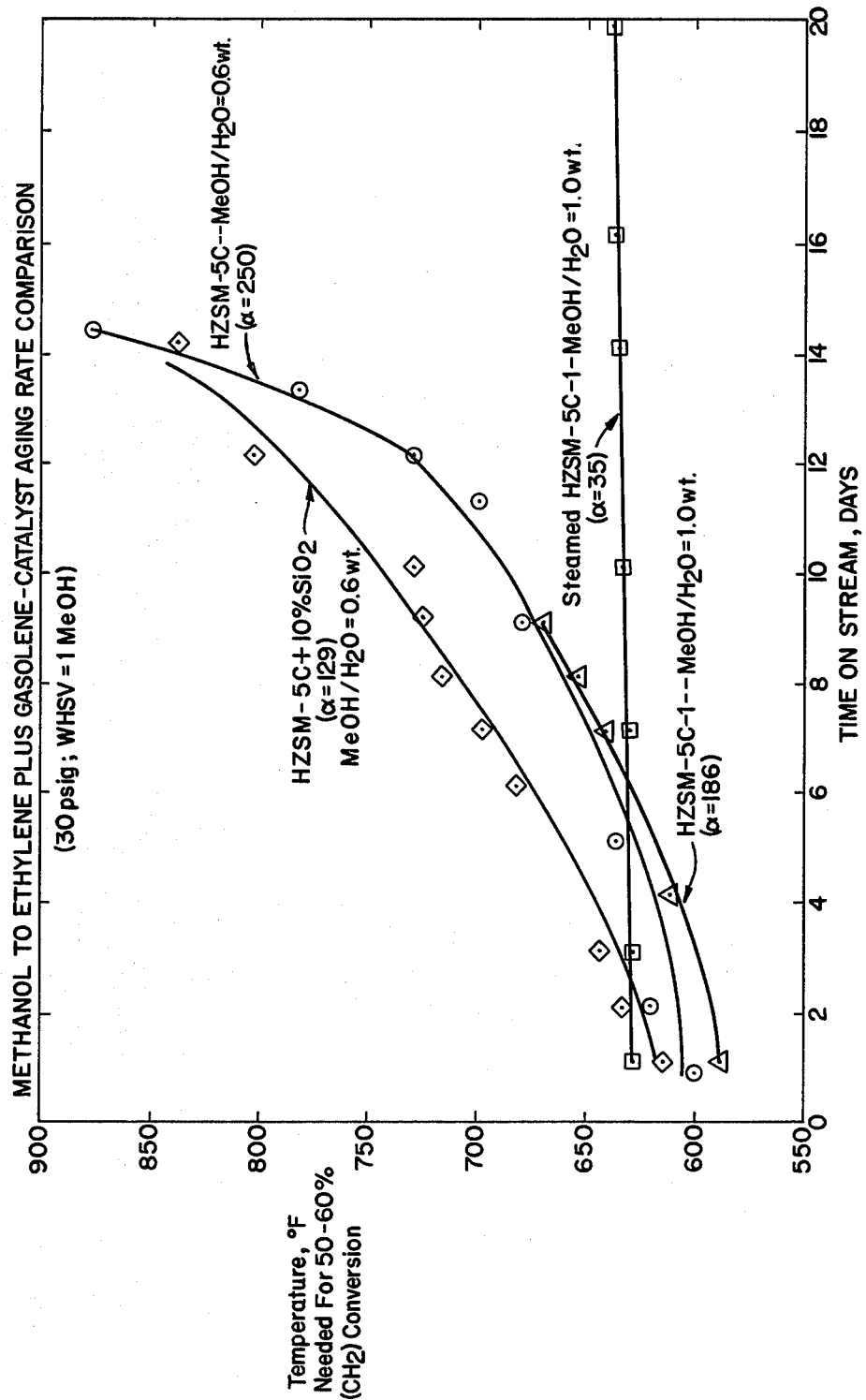

CATALYSTS FOR THE CONVERSION OF METHANOL TO ETHYLENE PLUS GASOLINE

BACKGROUND OF THE INVENTION

1. Field of the Invention

This invention is concerned with the conversion of a methanol feed to a hydrocarbon mixture of high ethylene content in the presence of an improved aluminosilicate zeolite catalyst. More particularly, this invention relates to a process for the conversion of methanol to ethylene plus gasoline in the presence of a specified crystalline aluminosilicate zeolite catalyst characterized by a crystal size of at least about 1 micron.

2. Description of the Prior Art

The increasing demand for inexpensive petrochemical raw materials such as ethylene has spurred efforts to provide efficient means for manufacturing ethylene from raw materials other than petroleum. Ethylene is a primary material source used in the manufacture of polyethylene and styrene monomers which are important to the production of synthetic fibers, plastics and petrochemicals. The principle raw material for ethylene at the present time is petroleum naphtha, which is steam cracked to produce a mixture of products from which ethylene is recovered.

Another source for the production of ethylene is methanol which is converted to olefins, including ethylene, and gasoline hydrocarbons in the presence of an aluminosilicate zeolite catalyst, such as ZSM-5. The factors which improve ethylene selectivity in the co-production of ethylene plus gasoline from methanol over zeolite catalysts include low diffusivity, low methanol partial pressure, dilution of the feed stream and partial methanol conversion.

For example, the highest ethylene selectivities in the co-production of ethylene plus gasoline from methanol over zeolite catalysts are achieved in the presence of small-pore crystalline aluminosilicate zeolites such as erionite and ZSM-34. Examples of this form of catalytic conversion can be found in U.S. Pat. Nos. 4,062,905 which discloses the use of erionite and 4,079,096 which discloses methanol conversion over ZSM-34. U.S. Pat. No. 4,062,905, also contains a broad teaching that catalysts used in the conversion of methanol can be subjected to thermal treatment, including steaming. It has been found, however, that these small-pore zeolites have the disadvantage of converting up to 15 to 20 percent of the methanol charge into coke. Additionally, the cycle times of these catalysts are only a few hours.

Another method of improving ethylene selectivity is to conduct the methanol conversion at sub-atmospheric partial pressure of reactant feed over an HZSM-5 as disclosed in U.S. Pat. No. 4,025,575.

Further methods of improving ethylene selectivity in the conversion of methanol over zeolite catalysts involve dilution of the reactant feed. U.S. Pat. No. 4,079,095 discloses the conversion of methanol and water in the presence of a catalyst comprising a crystalline aluminosilicate zeolite of the erionite-offretite family to a hydrocarbon product rich in ethylene and propylene. U.S. Pat. No. 4,083,888 discloses a process of converting a methanol feed to a hydrocarbon mixture of high ethylene content by catalytic contact of the feed in the presence of a substantially anhydrous diluent such as hydrogen, helium, nitrogen, carbon dioxide, lower alkanes and flue gas. The catalyst used is a crystalline aluminosilicate zeolite such as HZSM-5 having a crystallite size greater than about 0.5 micron. U.S. Pat. No. 4,083,889 describes a process of catalytic conversion of methanol in the presence of steam or water diluent over a ZSM-5 type catalyst in order to enhance ethylene production. The presence of the steam diluent induces sustained high catalytic activity with high selectivity for the formation of ethylene even at high conversion levels.

The diffusional characteristics of crystalline aluminosilicate zeolites can be moderated to increase ethylene yields upon the catalytic conversion of methanol. For example, U.S. Pat. No. 4,148,835 discloses a process for the catalytic conversion of methanol to light olefinic hydrocarbons with high selectivity for ethylene production by utilizing a crystalline aluminosilicate zeolite having a crystal size of at least about 1 micron. It has also been observed that silica-modified HZSM-5 also produces unusually high ethylene yields. The deposited silica within the pore structure of the zeolite limits diffusivity and results in an increase in ethylene selectivity compared to the parent zeolite. The intrasilica large crystal zeolite is somewhat less active than the parent zeolite which also is attributed to the silica "stuffing". However, even zeolites of large crystal size and the intrasilica version thereof suffer a serious deficiency in processing. Both have cycle times of only about 7 to 10 days, and require substantial daily increases in temperature, about 10° F. per day, to maintain a constant conversion of between about 50 and 60 percent.

U.S. Pat. No. 4,118,431 discloses a process for the conversion of methanol to gasoline boiling components in the presence of a catalyst in which the active catalyst particles are mixed with heat absorbing inert particles such that the alpha activity of the combined solids in the reactor falls in the range of about 20 to 50. The ratio of catalyst particles to heat absorbing inert particles is varied as a function of the catalyst activity and in an arrangement to particularly limit undesired exposure of the catalyst downstream of the reaction front to deactivation of catalyst particles by process formed steam. The addition of the inert solids to the process are disadvantageous in view of the increased handling problems and increased complexities which are added to the methanol conversion process.

BRIEF SUMMARY OF THE INVENTION

In accordance with the present invention a methanol feed is directly converted to a hydrocarbon mixture of high ethylene content in the presence of an aluminosilicate zeolite catalyst without the disadvantages of the prior art by controlling the alpha activity of the zeolite catalyst to within the range of about 6 to about 100. It has now been discovered that presteaming of the zeolite catalyst to an alpha activity in the range of about 6 to about 100 overcomes the instability of the catalyst while processing. Presteaming the catalyst also increases the cycle time to greater than about 3 weeks.

The present process involves conversion of a feed containing a lower monohydric alcohol having up to 4 carbon atoms by contact at elevated temperatures with a catalyst comprising a crystalline aluminosilicate zeolite having a crystal size of at least about 1 micron, usually in the approximate range of 1 to 20 microns and preferably 1 to 6 microns. The crystalline aluminosilicate zeolite is essentially characterized by a silica-to-alumina ratio of at least about 12 and a constraint index within the approximate range of 1 to 12. The zeolite catalyst is presteamed to the desired alpha activity. The reaction product mixture comprises light olefins with high selectivity for ethylene production and gasoline products.

BRIEF DESCRIPTION OF THE DRAWING

The drawing is a plot of the temperature needed to achieve 50 to 60 percent methanol conversion to ethylene plus gasoline versus the time on stream of four catalysts of varying alpha activity.

DESCRIPTION OF THE SPECIFIC EMBODIMENTS

It is contemplated that a feed comprising any monohydric alcohol having from 1 to 4 carbon atoms may be used as feed to the process of this invention. Thus, methanol, ethanol, n-propanol, isopropanol, n-butanol, sec-butanol and isobutanol may be used either alone or in admixture with one another. The particularly preferred feed is methanol.

In accordance with the present invention, such feed is brought into contact, under conversion conditions, with a catalyst comprising a crystalline aluminosilicate zeolite having a crystal size of at least about 1 micron, a silica-to-alumina ratio of at least about 12 and a constraint index within the approximate range of 1 to 12, the catalyst having been presteamed to an alpha activity within the range of about 6 to about 100, with an alpha activity of about 35 being the most desirable. Non-limiting examples of useful crystalline aluminosilicate zeolites include ZSM-5, ZSM-11, ZSM-12, ZSM-35 and ZSM-38.

The synthesis and characteristics of zeolite ZSM-5 are described in U.S. Pat. No. 3,702,886, issued Nov. 14, 1972, the disclosure of which is incorporated herein by reference.

The synthesis and characteristics of zeolite ZSM-11 are described in U.S. Pat. No. 3,709,979, issued Jan. 9, 1973, the disclosure of which is incorporated herein by reference.

The synthesis and characteristics of zeolite ZSM-12 are described in U.S. Pat. No. 3,832,449, issued Aug. 27, 1974, the disclosure of which is incorporated hereby by reference.

The synthesis and characteristics of zeolite ZSM-35 are described in U.S. Pat. No. 4,016,245, issued Apr. 5, 1977, the disclosure of which is incorporated herein by reference.

The synthesis and characteristics of zeolite ZSM-38 are described in U.S. Pat. No. 4,046,849, the entire contents of which are herein incorporated by reference.

The crystal size of the preferred crystalline aluminosilicate zeolites is at least about 1 micron, typically in the approximate range of 1 to 20 microns and particularly in the range of 1 to 6 microns. Certain preparation techniques result in these particularly large crystal size aluminosilicate zeolites. A method of preparation is described in U.S. patent application Ser. No. 304,725, filed Sept. 23, 1981, now U.S. Pat. No. 4,375,458, herein incorporated by reference.

Although the zeolites herein described have unusually low alumina contents, i.e., high silica-to-alumina ratios, they are very active even when the silica-to-alumina ratio exceeds 30. The activity is surprising since catalytic activity is generally attributed to framework aluminum atoms and cations associated with these aluminum atoms. These catalysts retain their crystallinity for long periods in spite of the presence of steam and high temperature which induces irreversible collapse of the framework of other zeolites, e.g., of the X and A type. Furthermore, carbonaceous deposits when formed, may be removed by burning at higher than usual temperature to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica-to-alumina ratio of at least about 12; and a structure providing constrained access to the crystalline free space.

The silica-to-alumina ratio referred to may be determined by conventional analysis. This ratio is meant to represent as closely as possible, the ratio in the rigid anionic framework of the zeolite crystal and to exclude aluminum in the binder or in cationic or other form within the channels. Although catalysts with a silica-to-alumina ratio of at least 12 are useful, it is preferred to use catalysts having higher ratios of at least about 30. Such catalysts, after activation, acquire an intracrystalline sorption capacity for normal hexane which is greater than that for water, i.e., they exhibit "hydrophobic" properties. It is believed that this hydrophobic character is advantageous in the present invention.

The type of zeolites useful in this invention freely sorb normal hexane and have a pore dimension greater than about 5 Angstroms, or, if elliptical in pore shape, at least the size of the pores of ZSM-5. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section of normal hexane is excluded and the zeolite is not of the desired type. Windows of 10-membered rings are preferred, although, in some instances, excessive puckering or pore blockage may render these catalysts ineffective. 12-membered rings do not generally appear to offer sufficient constraint to produce the advantageous conversions. Also, structures can be conceived due to pore blockage or other cause, that may be operative.

Rather than attempt to judge from the crystal structure whether or not a catalyst possesses necessary constrained access, a simple determination of the "constraint index" may be made by passing continuously a mixture of an equal rate of normal hexane and 3-methylpentane over a small sample, approximately 1 gram or less of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950 F. to give an overall conversion between 10% and 60%. The mixture of hydrocarbons is passed at 1 liquid hourly space velocity (i.e., 1 volume of liquid hydrocarbon per volume of catalyst per hour) over the catalyst with the helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are:

| Crystalline Aluminosilicate | CI |
| --- | --- |
| ZSM-5 | 8.3 |
| ZSM-11 | 8.7 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F. for 1 hour, followed by base exchange with ammonium salts and by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica-to-alumina ratio of at least about 12 and a dried crystal density of not less that about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal, or in mercury under pressure (mercury porosimeter). It is possible that the unusual sustained activity and stability of this class of zeolite is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

|  | Void | Framework |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The catalyst composition useful in this invention may be in the form of compacted pellets, or extrudate particles with a diameter, for example of ⅛ inch or ¼ inch; or in the form of beads; or in the form of fine particles of about 50 microns diameter suitable for fluidization. The particular form chosen is determined by the type of catalyst bed to be used, which may be a fixed compact bed, a fixed fluidized bed, or a variety of transport bed. In any case, the crystalline aluminosilicate zeolite component of the catalyst composition may be blended with a binder such as alumina or silica-alumina to form the above-described particles by methods well known to those skilled in the art of catalyst preparation. As noted above, the specific zeolites useful in the catalyst compositions of this invention may require activation by base exchange with ammonium salts and calcination in air. These steps may be done before or after pelletizing or extruding to form the desired catalyst particles. Regardless of when these steps are effected, the catalyst composition useful in this invention consists essentially of a crystalline aluminosilicate zeolite having the above-described characteristics and at least partially in the hydrogen form. Of the enumerated zeolites, HZSM-5, which is in the hydrogen form, is preferred. Particularly preferred because of its enhanced effectiveness is HZSM-5 having a crystalline size greater than about 1 micron, said crystalline size referring to a weighted average. In addition, an intrasilica/ZSM-5 zeolite may be used. Silica-modified HZSM-5 has been shown to produce a few percent increase in ethylene selectivity from the conversion of methanol.

The methanol feed is passed over the catalyst at a rate of 0.2 to 20 WHSV (weight hourly space velocity), preferably at 0.5 to 5.0 WHSV. In all cases, the WHSV is calculated on the pounds of methanol feed per hour per weight of catalyst. For purposes of this invention, the methanol feed is contacted with the catalyst at a pressure of 1 to 10 atmospheres absolute, i.e. at a pressure of 0 to 135 psig. It is preferred, however, to conduct the reaction at from 0 to about 50 psig. It is important for purposes of this invention to maintain the reaction temperature as low as is consistent with the desired conversion per pass, this temperature being maintained at 500° F. to 750° F., and preferably within the range of 525° F. to about 650° F. Temperatures referred to herein are to be understood to refer to the maximum temperature within the reaction zone. Thus, in a fixed-bed operation, the inlet temperature may be lower than 500° F. Within the prescribed conditions, a conversion per pass of from 40% to about 90% of the methanol is achieved and the hydrocarbon mixture formed contains at least 25 weight percent ethylene.

The term "conversion," as used herein, is to be understood to mean a chemical change in which a hydrocarbon having at least 2 carbon atoms is formed. Thus, a substantially pure methanol feed will form a hydrocarbon mixture and also some dimethyl ether. This dimethyl ether is ignored in computing conversion since no new carbon to carbon bonds form in its formation. If some dimethyl ether is present in the methanol feed, its conversion to hydrocarbons is added to that of the methanol to arrive at a "conversion" value. Specifically, 50% conversion as used herein means that 50% of the total —$CH_2$— groups present in the methanol and dimethyl ether of the methanol feed is converted to hydrocarbons.

Alpha values or alpha activity is a measure of normal hexane cracking conversion relative to a silica-alumina cracking catalyst and the alpha test is described in a Letter to the Editor entitled "Superactive Crystalline Aluminosilicate Hydrocarbon Cracking Catalysts" by P. B. Weisz and J. N. Miale, *Journal of Catalysis*, Vol. 4, No. 4, August 1965, pp. 527–529, said article being incorporated by reference.

The acidic zeolites, prior to steaming in accordance with the present invention, have an alpha value in excess of 150.

Steaming is carried out in order to reduce the alpha activity to the ranges previously set forth.

Preferably, steaming is carried out at elevated temperatures ranging from about 350° F. to 1500° F. at either atmospheric or elevated pressures. The steaming can be carried out in atmospheres of 100 percent steam or an atmosphere of steam and inert gas. The exact reduction in alpha activity is a function of steam partial pressure, temperature and time. None of these variables is critical per se and the only requirement is that the steaming be carried out in order to obtain the critical range of alpha values.

The following example illustrates the advantages of the present invention and serves to illustrate how the objectives of the present invention are obtained.

EXAMPLE

Four crystalline aluminosilicate zeolite catalysts were individually tested by charging the catalysts into a reactor which was fed with a mixture of water and methanol. The reaction conditions were varied for each catalyst to maintain methanol conversion at least about 50% as indicated in Table I. Each of the catalysts utilized had a crystal size of at least 1 micron. Three of the four catalysts had an alpha activity greater than 100. The fourth catalyst was presteamed and after steaming had an alpha activity of 35.

TABLE I

| Data at 30 psig Catalyst | HZSM-5 | | Intrasilica/ZSM-5 | | HZSM-5Cl | | Steamed HZSM-5Cl | |
|---|---|---|---|---|---|---|---|---|
| Alpha Charge | 200 | | 129 | | 186 | | 35 | |
| $H_2O$/MeOH (Wt) | 1.7 | | 1.7 | | 1.0 | | 1.0 | |
| WHSV (MeOH) | 1.0 | | 1.0 | | 1.0 | | 1.0 | |
| Reaction Temp., °F. | 613 | 730 | 615 | 726 | 589 | 670 | 628 | 639 |
| Stream Time, Days | 1.1 | 13.5 | 1.1 | 9.2 | 1.1 | 9.1 | 1.1 | 21.1 |
| % MeOH Conv. (to HC) | 64 | 46 | 51 | 65 | 54 | 48 | 59 | 58 |
| Products (Wt % HC) | | | | | | | | |
| $C_1 + C_2$ | 0.5 | 1.5 | 0.5 | 0.7 | 0.8 | 1.6 | 0.9 | 0.8 |
| $C_2=$ | 28.1 | 27.6 | 30.8 | 27.6 | 25.0 | 29.9 | 26.9 | 26.9 |
| ($C_2=-C_4=$) | 47.6 | 55.5 | 62.3 | 60.7 | 41.8 | 54.2 | 50.1 | 49.1 |
| $C_5^+$ Gasoline | 40.3 | 37.3 | 26.8 | 37.3 | 46.0 | 37.0 | 40.6 | 41.9 |

From Table I it can be clearly seen that the pre-steamed catalyst remained stable even after over 21 days on stream. The conversion of methanol to hydrocarbons remained about the same and product selectivities also remained substantially constant. The catalysts tested which had an alpha activity greater than 100 had a substantially different product selectivity when the time on stream was increased.

The improvement over the prior art is predicated by the discovery that by presteaming the large-crystal zeolite catalyst to an alpha activity between 6–100, the above-mentioned catalyst deficiency such as instability during processing and attendant short cycle times are overcome. It has been found that the presteamed large-crystal zeolite catalysts can increase cycle time to generally greater than about 3 weeks in addition to maintain a constant methanol conversion rate of between 50% to 60% without substantial daily increases in temperature. Also, product selectivities remain constant throughout the time the catalyst was on stream. Ethylene selectivity remains at greater than 20% by weight.

Referring to the FIGURE, it can be seen that unsteamed catalysts having an alpha activity greater than 100 require substantial increases in reaction temperature to maintain a methanol conversion rate between about 50% to 60%. The pre-steamed catalyst does not require this temperature increase. The increased cycle time coupled with the enhanced catalyst stability during processing of the presteamed catalyst of the present invention will enable a much easier development of a fixed-bed process for the co-production of ethylene plus gasoline from methanol than prior art catalysts.

What is claimed is:

1. In a process of converting methanol to ethylene plus gasoline by contacting methanol with an acidic crystalline aluminosilicate zeolite catalyst having a silica-alumina ratio of at least 12, a constraint index within the range of 1–12 and a crystal size of at least 1 micron, under conditions whereby a hydrocarbon mixture is formed containing at least about 25 wt.% ethylene, the improvement which comprises steaming said zeolite catalyst to adjust the alpha activity of said catalyst prior to use to within the range of 6–100 such as to increase catalyst cycle time and maintain a constant methanol conversion rate of between 50% to about 60% without substantial daily increases in temperature.

2. The process of claim 1 wherein the initial alpha activity of said zeolite is reduced to an alpha value of about 35.

3. The process of claim 1 wherein said zeolite is ZSM-5.

4. The process of claim 2 wherein said zeolite is ZSM-5.

5. The process of claim 1 wherein the zeolite is HZSM-5.

6. The process of claim 2 wherein the zeolite is HZSM-5.

7. The process of claim 1 wherein the zeolite is ZSM-5 having deposited silica within the pore structure of said zeolite.

8. The process of claim 2 wherein the zeolite is ZSM-5 having deposited silica within the pore structure of said zeolite.

9. The process of claim 1 wherein the initial alpha activity of said catalyst was greater than 100.

10. The process of claim 1 wherein said catalyst is kept on stream for at least about 21 days.

* * * * *

UNITED STATES PATENT AND TRADEMARK OFFICE
CERTIFICATE OF CORRECTION

PATENT NO. : 4,480,145

DATED : October 30, 1984

INVENTOR(S) : J. A. Brennan, S. J. Lucki and H. J. Schoennagel

It is certified that error appears in the above-identified patent and that said Letters Patent is hereby corrected as shown below:

Col. 10, lines 3-4, change "silica-alumina" to --silica-to-alumina--

Signed and Sealed this

Twenty-eighth Day of May 1985

[SEAL]

Attest:

DONALD J. QUIGG

Attesting Officer

Acting Commissioner of Patents and Trademarks